United States Patent
Noda et al.

(10) Patent No.: US 8,343,123 B2
(45) Date of Patent: Jan. 1, 2013

(54) ABSORBENT ARTICLE

(75) Inventors: Yuki Noda, Kagawa (JP); Kenichiro Kuroda, Kagawa (JP); Kumiko Nishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 205 days.

(21) Appl. No.: 12/516,870

(22) PCT Filed: Dec. 12, 2007

(86) PCT No.: PCT/JP2007/073973
§ 371 (c)(1),
(2), (4) Date: May 29, 2009

(87) PCT Pub. No.: WO2008/072675
PCT Pub. Date: Jun. 19, 2008

(65) Prior Publication Data
US 2010/0069874 A1  Mar. 18, 2010

(30) Foreign Application Priority Data

Dec. 13, 2006 (JP) ................................. 2006-336188

(51) Int. Cl.
*A61F 13/15* (2006.01)
(52) U.S. Cl. ....... 604/385.01; 604/385.101; 604/385.19; 604/385.201; 604/385.23
(58) Field of Classification Search ............. 604/385.23, 604/385.201, 385.19, 385.01, 385.101
See application file for complete search history.

(56) References Cited

U.S. PATENT DOCUMENTS

| | | | | |
|---|---|---|---|---|
| 6,458,111 B1 * | 10/2002 | Onishi et al. | ............. | 604/385.01 |
| 7,067,711 B2 * | 6/2006 | Kuroda et al. | ................ | 604/380 |
| 7,132,585 B2 * | 11/2006 | Kudo et al. | ................... | 604/380 |
| 2004/0210204 A1 | 10/2004 | Shimada et al. | | |
| 2006/0058761 A1 | 3/2006 | Kudo et al. | | |
| 2006/0142726 A1 | 6/2006 | Tokumoto et al. | | |
| 2007/0233029 A1 * | 10/2007 | Jansson et al. | ................ | 604/380 |

FOREIGN PATENT DOCUMENTS

| | | |
|---|---|---|
| CN | 1761440 | 4/2006 |
| JP | 2003-010244 A | 1/2003 |
| JP | 2004-081618 A | 3/2004 |
| JP | 2004-154154 A | 6/2004 |
| JP | 3566012 B2 | 6/2004 |

(Continued)

OTHER PUBLICATIONS

International Search Report of Application No. PCT/JP2007/073973 mailed Jan. 15, 2008.

(Continued)

*Primary Examiner* — Lynne Anderson
*Assistant Examiner* — Bradley Philips
(74) *Attorney, Agent, or Firm* — Lowe Hauptman Ham & Berner, LLP

(57) ABSTRACT

An absorbent article comprising an absorbent body, wherein the absorbent body has multiple linear or curved fold regions with a flexural rigidity lower than average flexural rigidity and with a flexural rigidity lower than that in adjacent regions. Accordingly, there is provided an absorbent article that can change its morphology along the configuration of wear object. Absorbent article has multiple linear or curved first fold regions with a flexural rigidity lower than the average flexural rigidity of the absorbent article and with a flexural rigidity lower than that in adjacent regions, which multiple first fold regions are provided in approximately symmetric relationship with respect to the center line in the direction of width.

17 Claims, 14 Drawing Sheets

FOREIGN PATENT DOCUMENTS

| | | |
|---|---|---|
| JP | 2005-168832 A | 6/2005 |
| JP | 2006-061396 A | 3/2006 |
| JP | 2007-007283 A | 1/2007 |
| JP | 2007-037660 A | 2/2007 |
| JP | 2008-246088 A | 10/2008 |
| JP | 2008-246089 A | 10/2008 |
| WO | 02/094153 A1 | 11/2002 |
| WO | 2006025934 | 3/2006 |
| WO | 2006059922 | 6/2006 |

OTHER PUBLICATIONS

Extended European Search Report issued to European Application No. EP07859793.7, mailed May 31, 2012.

Office Action issued to Chinese Application No. 200780045633.2, mailed Dec. 16, 2011.

* cited by examiner

ABSORBENT ARTICLE

RELATED APPLICATIONS

The present application is based on International Application Number PCT/JP2007/073973, filed Dec. 12, 2007, and claims priority from Japanese Application Number 2006-336188, filed Dec. 13, 2006, the disclosures of which are hereby incorporated by reference herein in their entirety.

TECHNICAL FIELD

The present invention relates to an absorbent article.

BACKGROUND ART

Conventionally, various improvements have been made to absorbent articles, such as sanitary napkins, to allow for bending along the wearer's body shape to prevent discharged matter such as menstrual blood from leaking out.

For example, an absorbent article has been proposed including a compressed groove formed on a skin contacting side, from a central portion in a longitudinal direction of the absorbent article to a back portion that is disposed on a back side of a wearer during use, so as to approach side edges of the back portion as an end edge of the back portion is approached. The compressed groove is disposed to be separated from the end edge and the side edges, and includes a convex portion in a central portion in the longitudinal direction, which is projected forward, as disclosed in Japanese Patent No. 3566012 (hereinafter referred to as Patent Document 1).

DISCLOSURE OF THE INVENTION

Problems to be Solved by the Invention

In the absorbent article disclosed in Patent Document 1, the compressed groove forms the convex portion that is projected forward in a central portion of the absorbent article, while inducing deformation by making a density greater and a thickness smaller than a periphery thereof by way of embossing. However, stiffness of the compressed groove, which has a high density due to the embossing, is extremely high and requires a high load in order to be bent. As a result, in a case where a wearer wears normal underwear having a low contractile force (squeezing force), the absorbent article does not deform along with wearer's body shape, and thus the wearer may feel a foreign-body sensation and menstrual blood and the like may leak from a gap generated thereby.

An objective of the present invention is to provide an absorbent article including an absorbent core that can deform along with a shape of an applied part, by forming a plurality of bending regions of a linear shape or a curved shape on the absorbent core, which have a bending stiffness less than an average bending stiffness of the absorbent core and less than a bending stiffness of an adjacent region.

Means for Solving the Problems

In a first aspect of the present invention, an absorbent article having a width direction and a longitudinal direction that is orthogonal to the width direction, includes: a top sheet that is at least partially liquid permeable; a back sheet that is liquid impermeable; an absorbent core that has an elongated shape and is disposed between the top sheet and the back sheet along the longitudinal direction, in which the absorbent core includes a plurality of first bending regions having a bending stiffness less than an average bending stiffness of the absorbent core and less than a bending stiffness of an adjacent region, and the plurality of first bending regions is formed to be substantially symmetrical across a center line equally dividing the absorbent article in the width direction.

According to a second aspect of the present invention, in the absorbent article as described in the first aspect, the plurality of first bending regions are formed dominantly in at least one end portion in the longitudinal direction.

According to a third aspect of the present invention, in the absorbent article as described in the first or the second aspect, in at least an end of the absorbent core in the longitudinal direction, the plurality of first bending regions include a first bending region that is disposed such that an end thereof on a central side in the longitudinal direction is located on an outer side in the width direction and an end thereof on an outer side in the longitudinal direction is located on a central side in the width direction.

According to a fourth aspect of the present invention, the absorbent article as described in any one of the first to the third aspects includes a plurality of second bending regions that are formed so as to intersect with the center line in the width direction and have a predetermined width in the longitudinal direction, in which a region that is interposed between the second bending regions adjacent to each other in the longitudinal direction can be displaced in the longitudinal direction.

Effects of the Invention

According to the present invention, an absorbent article including an absorbent core can be provided, which can deform along with a shape of an applied part, by forming a plurality of bending regions of a linear shape or a curved shape on the absorbent core that have a bending stiffness less than an average bending stiffness of the absorbent core and less than a bending stiffness of an adjacent region.

PREFERRED MODE FOR CARRYING OUT THE INVENTION

The preferred embodiments for implementing the present invention are described hereinafter with reference to the drawings.

Figure 1A:
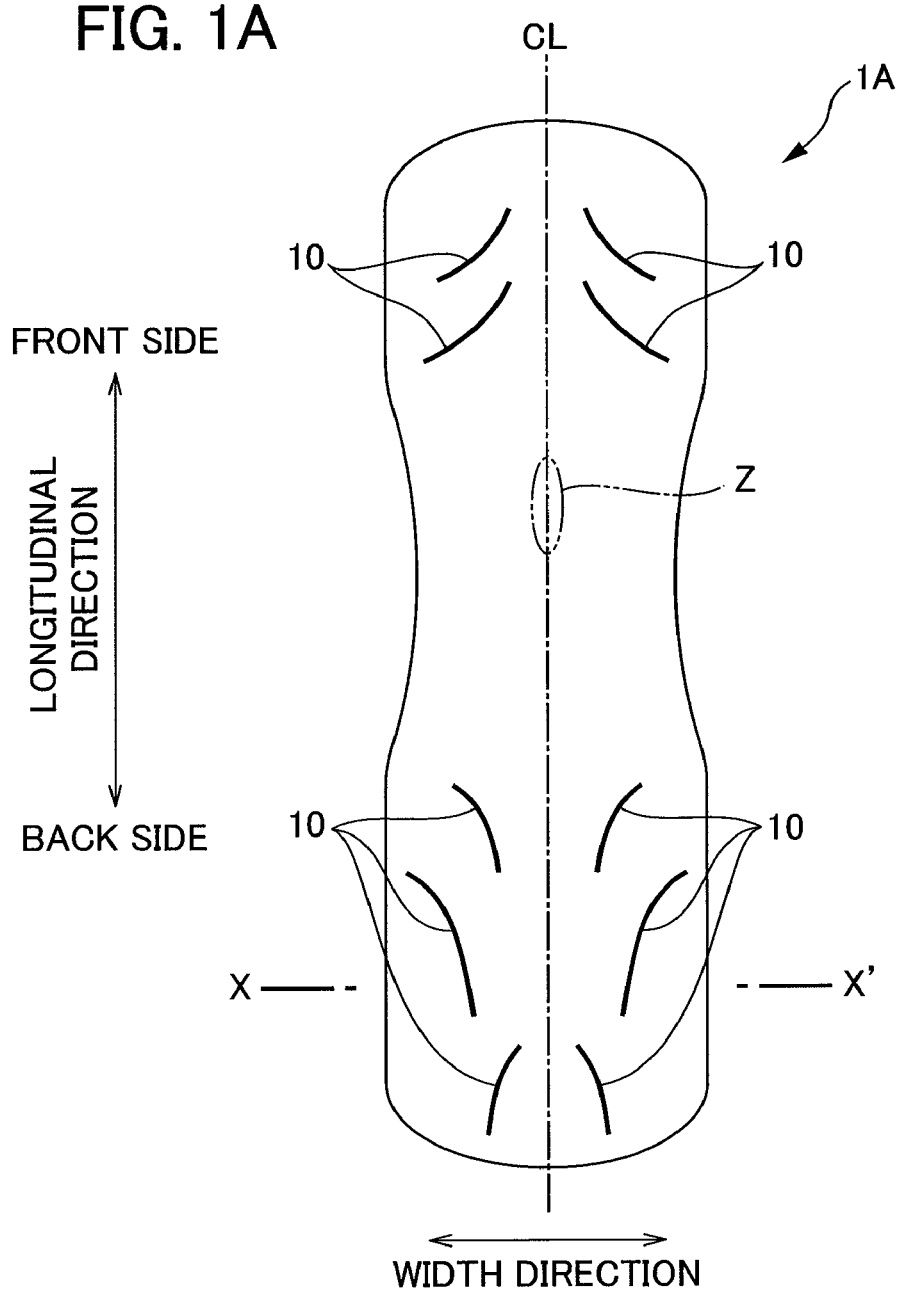
FIG. 1A is a plan view of an absorbent core according to a first embodiment of the present invention.
Figure 1B:
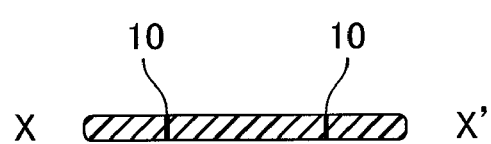
FIG. 1B is a cross-sectional view of the absorbent core according to the first embodiment of the present invention.
Figure 2A:
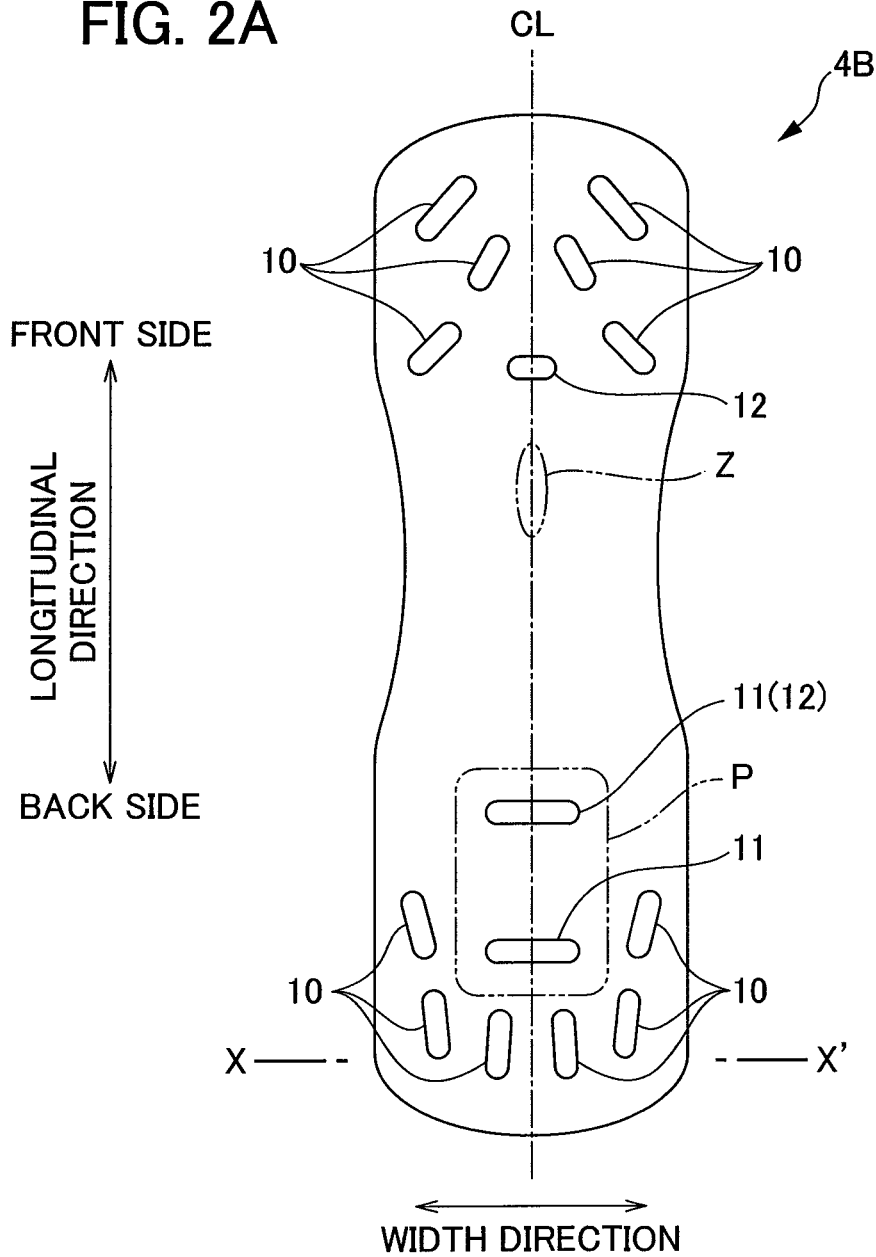
FIG. 2A is a plan view of an absorbent core according to a second embodiment of the present invention.
Figure 2B:
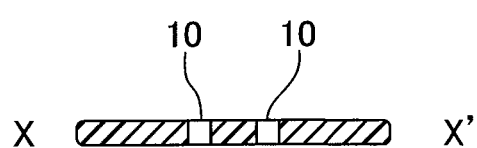
FIG. 2B is a cross-sectional view of the absorbent core according to the second embodiment of the present invention.
Figure 3:
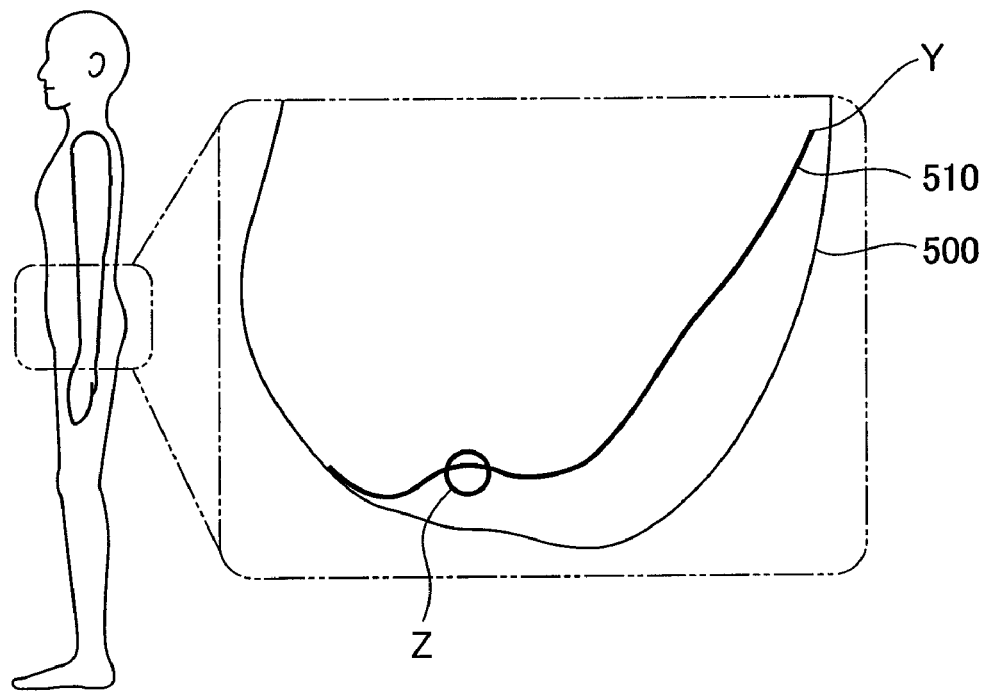
FIG. 3 is a diagram showing a cross-sectional shape of a human body taken by MRI.
Figure 4:
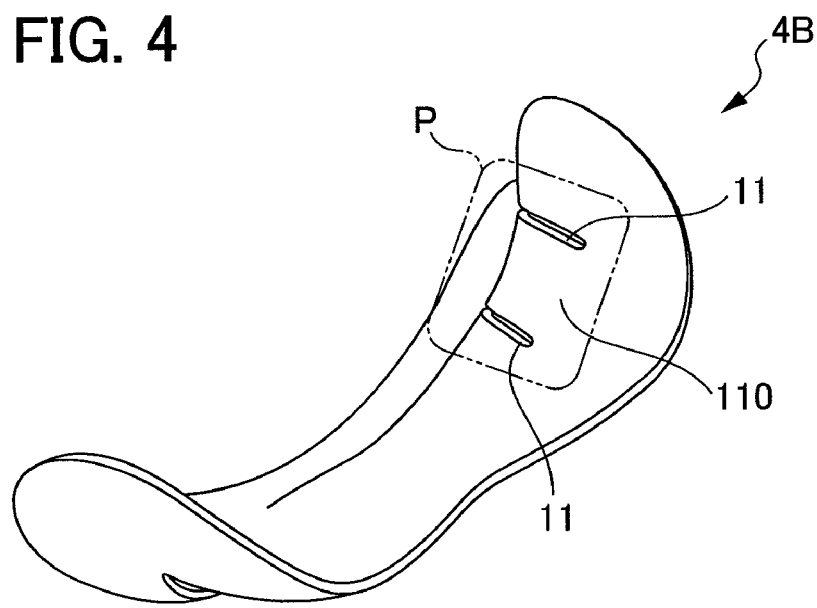
FIG. 4 is a diagram illustrating the absorbent core in use according to the second embodiment of the present invention.
Figure 5A:
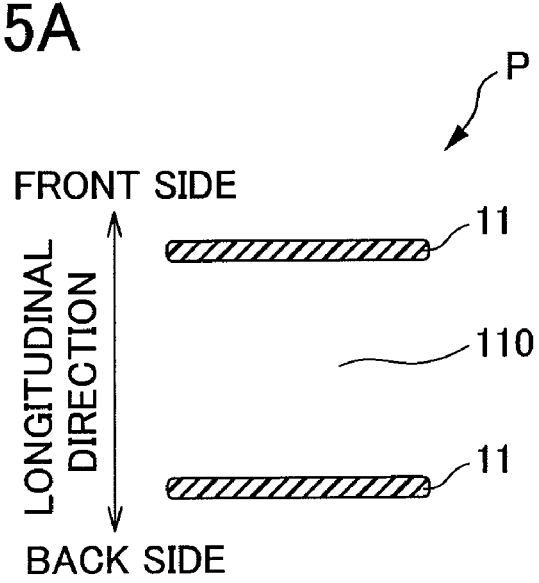
FIG. 5A is a partially enlarged view of a region P in FIG. 4.
Figure 5B:
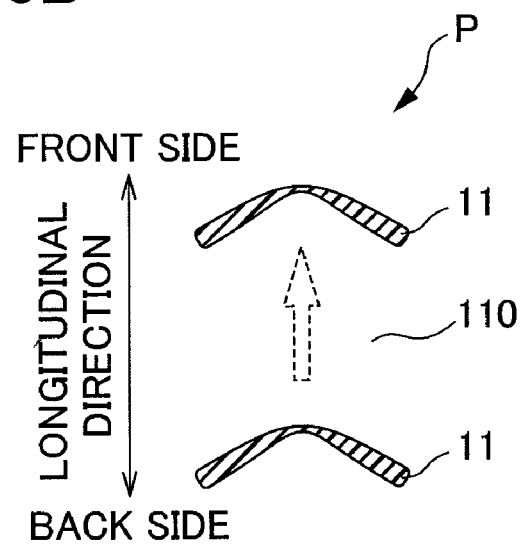
FIG. 5B is an enlarged view of a region P in FIG. 4.
Figure 6A:
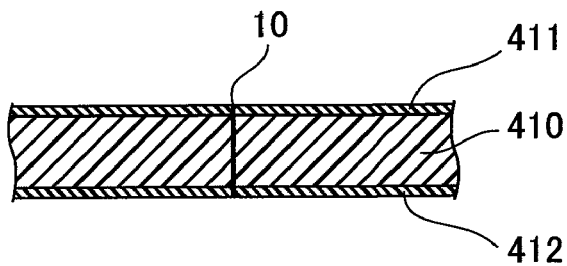
FIG. 6A is a cross-sectional view of the absorbent core.
Figure 7A:
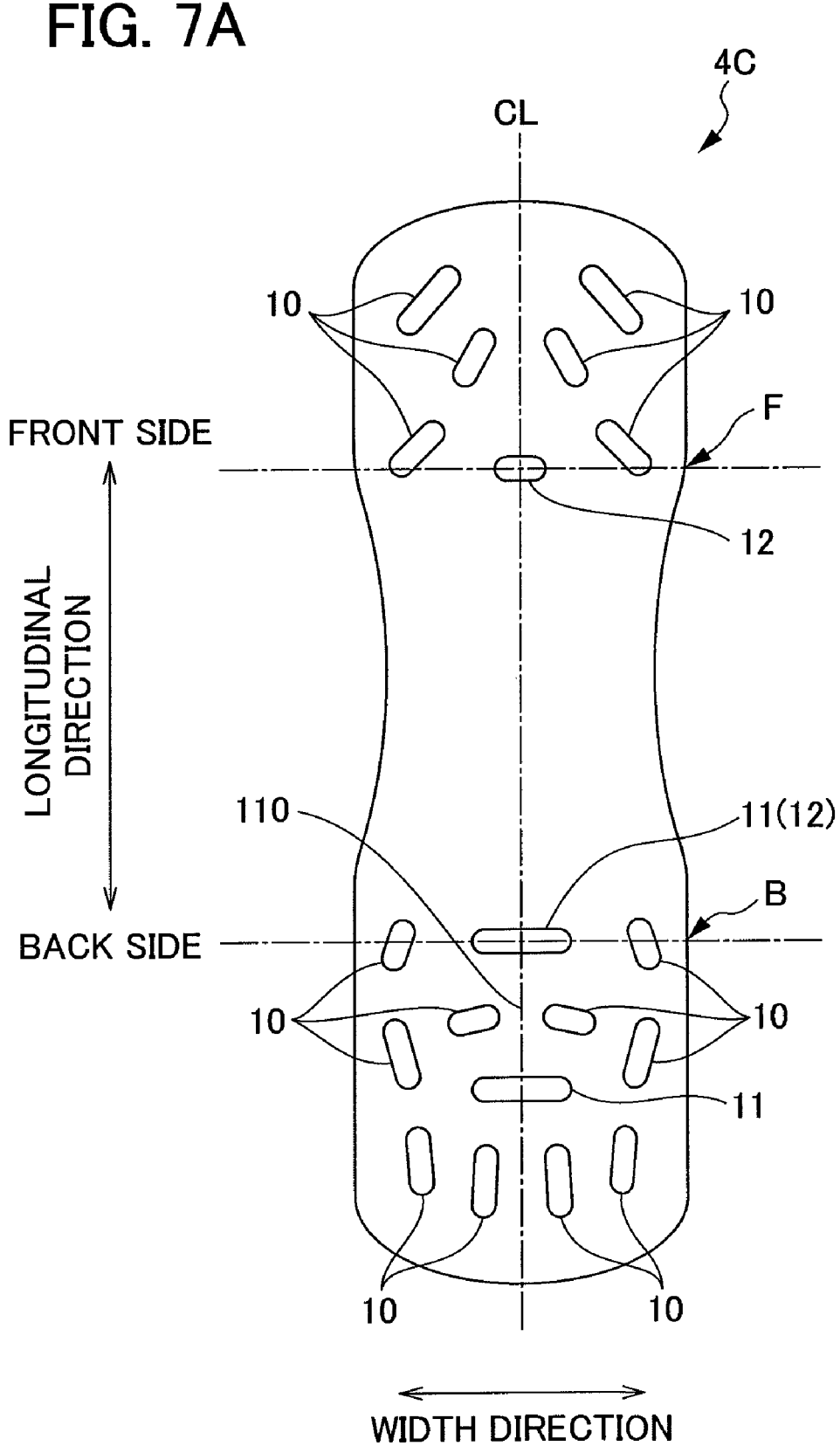
FIG. 7A is a plan view of an absorbent core according to a third embodiment.
Figure 7B:
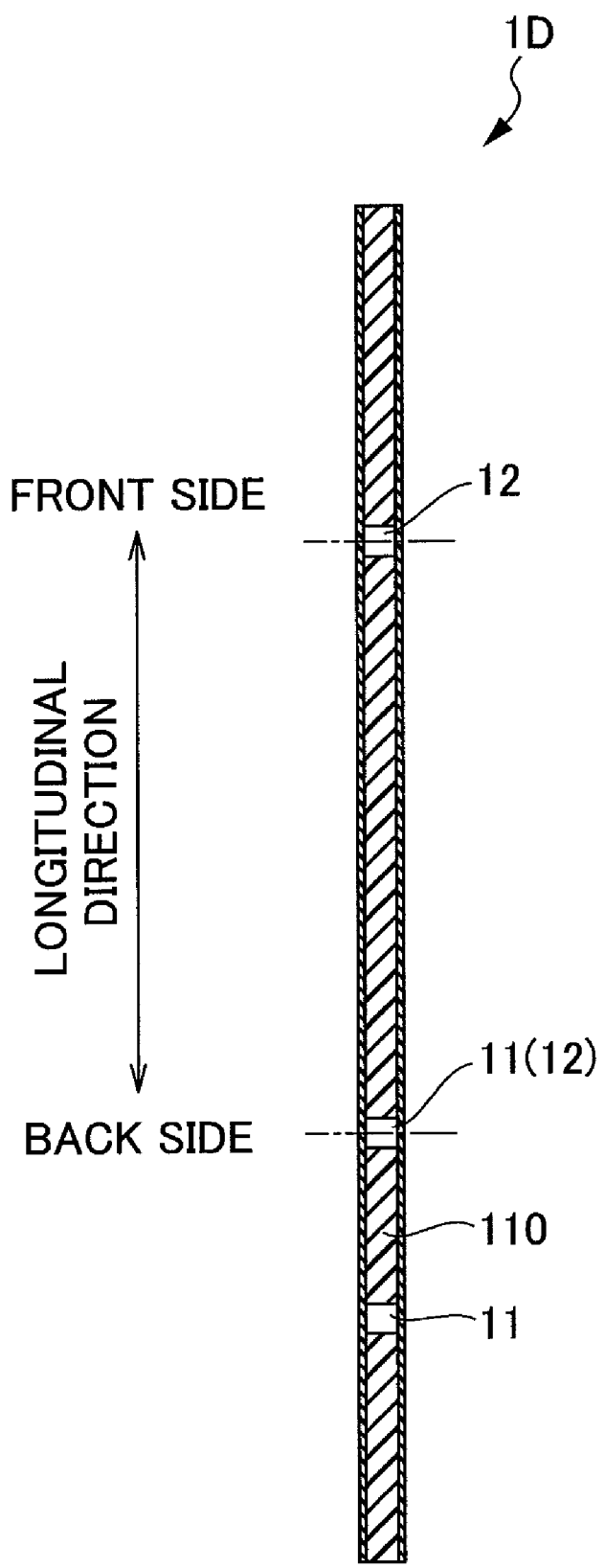
FIG. 7B is a cross-sectional view of an absorbent core according to the third embodiment.
Figure 8:
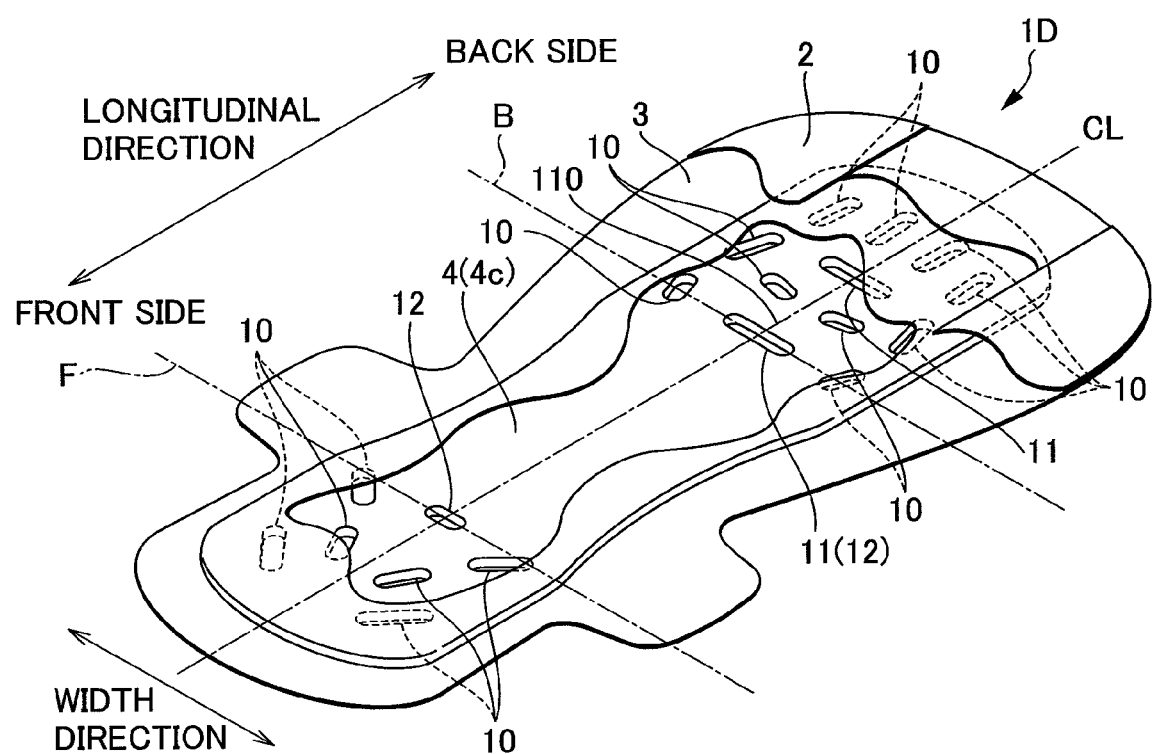
FIG. 8 is a diagram illustrating an absorbent article according to the present invention including the absorbent article according to the third embodiment.
Figure 9:
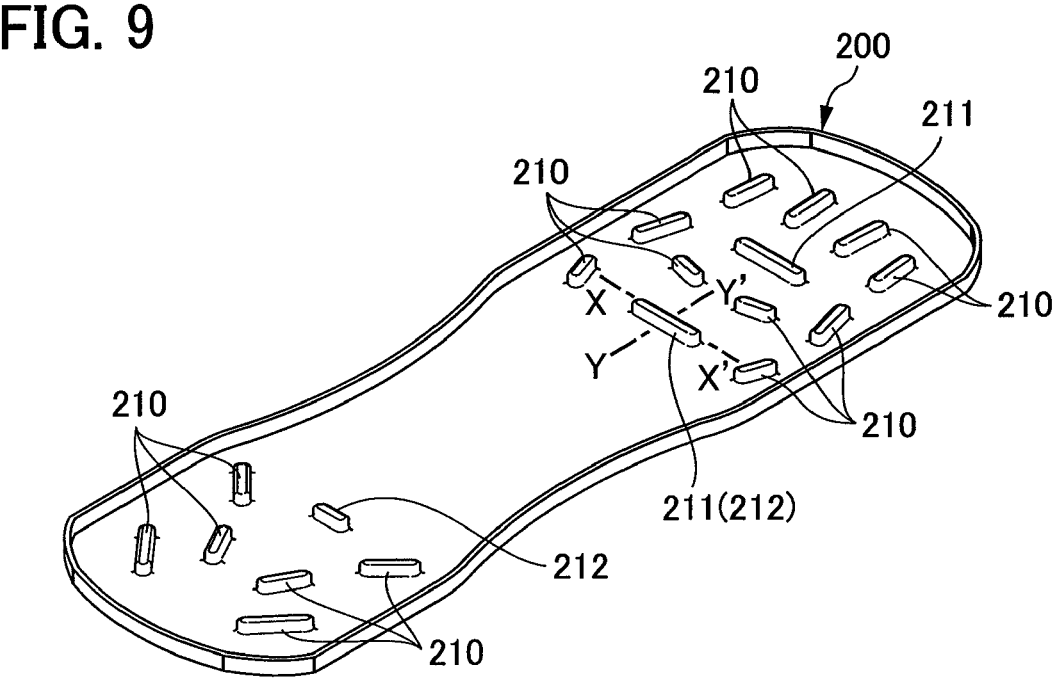
FIG. 9 is a perspective view of a meshed container 200.
Figure 10:
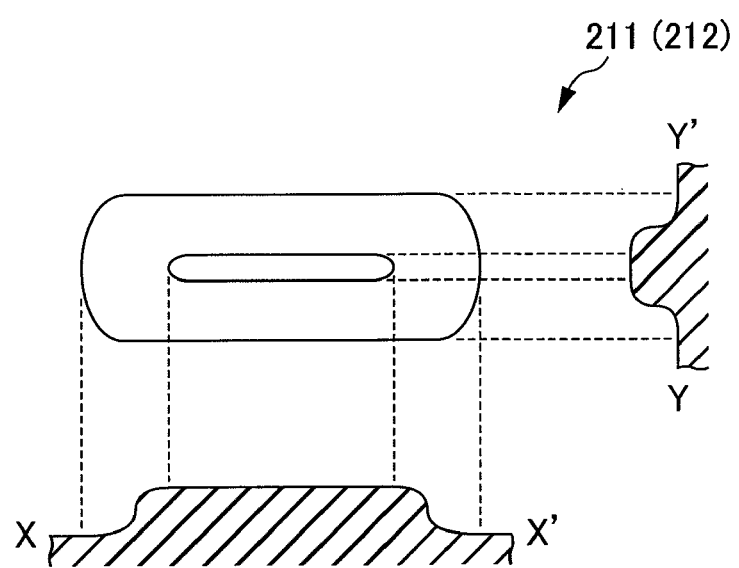
FIG. 10 is a diagram illustrating a shape of a convex portion formed in the meshed container 200.
Figure 11:
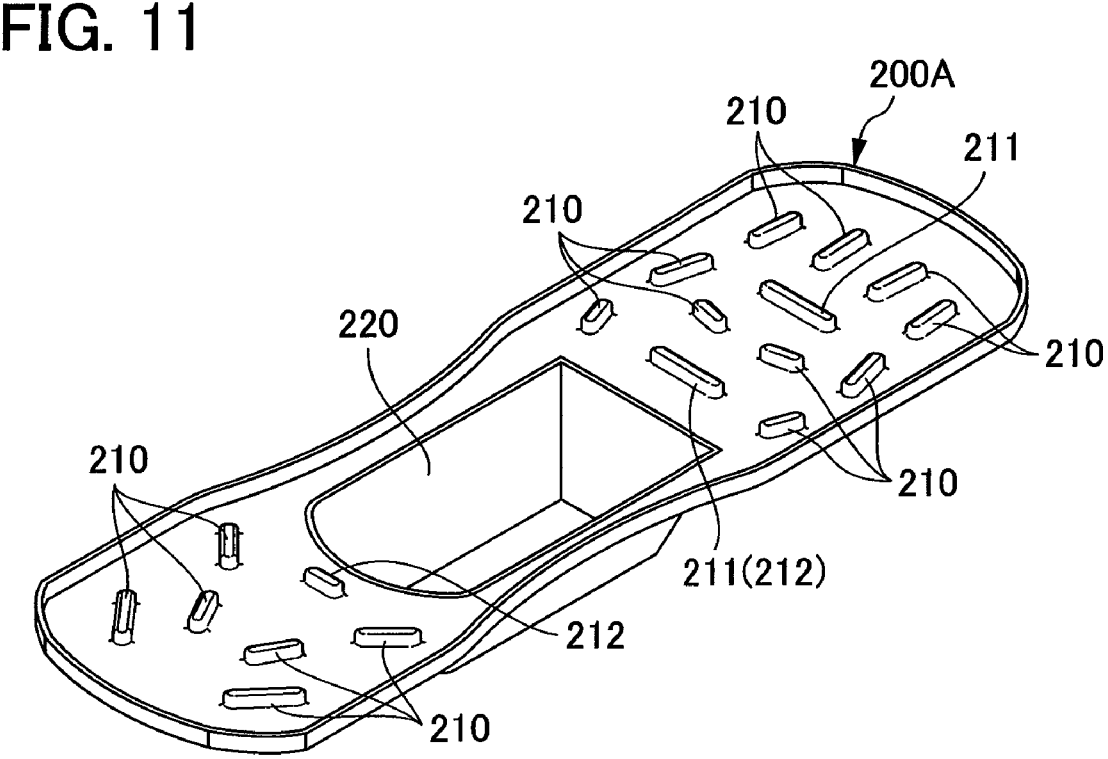
FIG. 11 is a perspective view of a meshed container 200A.
Figure 12:
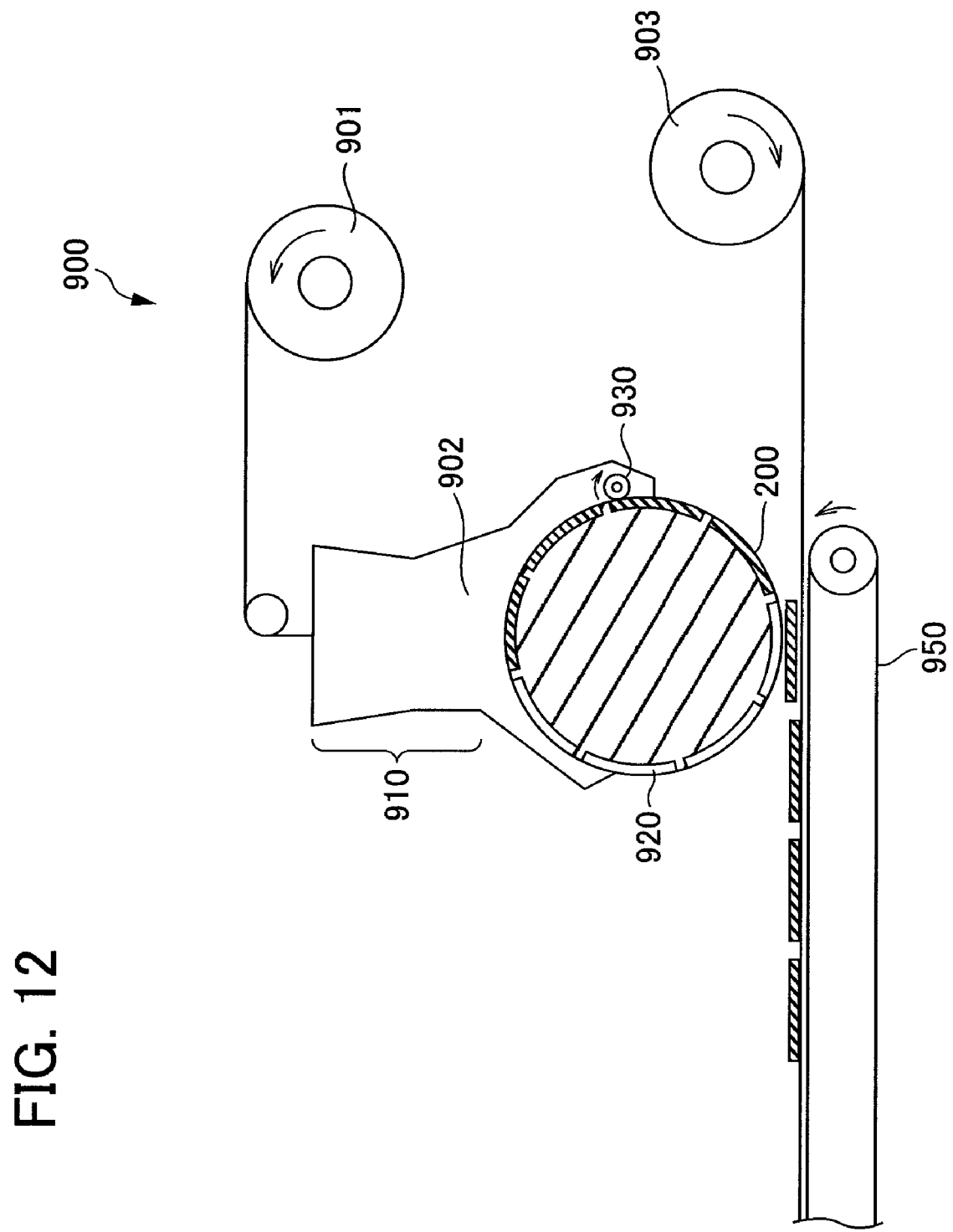
FIG. 12 is an example of a manufacturing device of the absorbent core used in the absorbent article according to the present invention.
Figure 13:
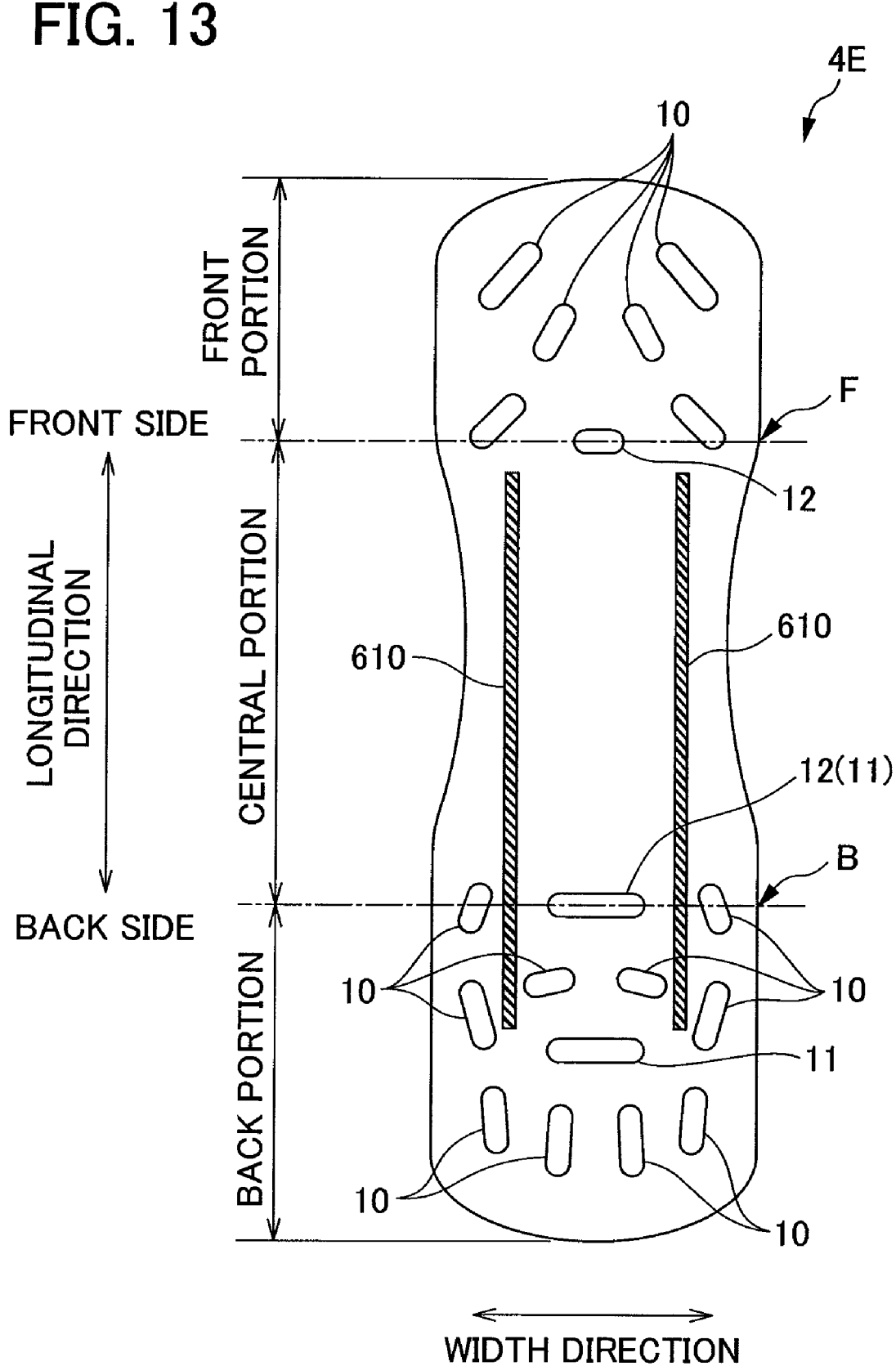
FIG. 13 is a plan view of an absorbent core according to a modification of the third embodiment.
Figure 14:
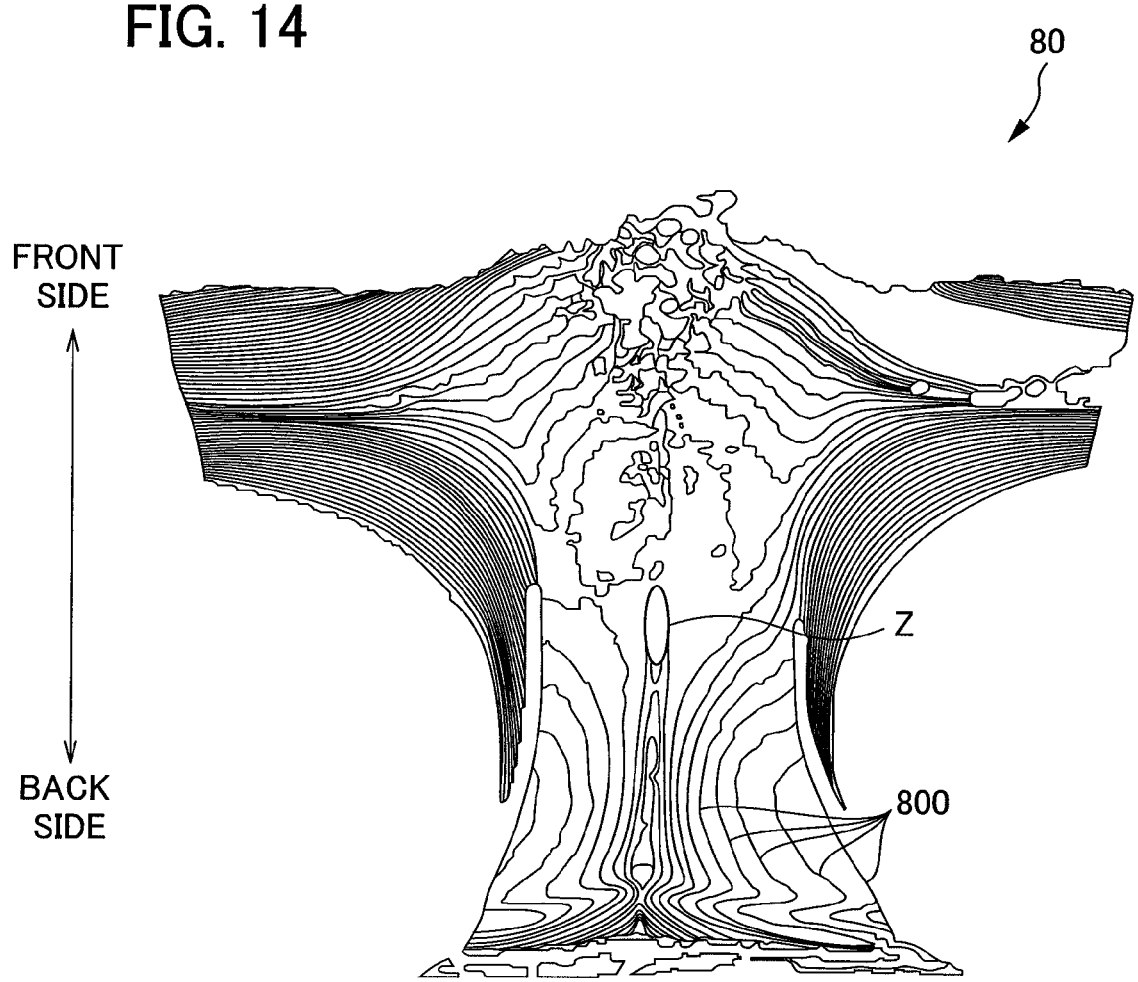
FIG. 14 is a 3-D contour plot of a groin area of an adult woman.

FIGS. 1A and 1B are a plan view and a cross-sectional view of an absorbent core according to a first embodiment of the present invention, respectively. FIGS. 2A and 2B are a plan view and a cross-sectional view of an absorbent core according to a second embodiment of the present invention, respectively. FIG. 3 is a diagram showing a cross-sectional shape of a human body taken by MRI. FIG. 4 is a diagram illustrating the absorbent core in use according to the second embodiment of the present invention. FIGS. 5A and 5B are enlarged views of a region P in FIG. 4. FIGS. 6A to 6F are cross-sectional views of various absorbent cores. FIGS. 7A and 7B are a plan view and a cross-sectional view of an absorbent core according to a third embodiment, respectively. FIG. 8 is a diagram illustrating an absorbent article according to the present invention including the absorbent article according to the third embodiment. FIG. 9 is a perspective view of a meshed container 200. FIG. 10 is a diagram illustrating a shape of a convex portion formed in the meshed container 200. FIG. 11 is a perspective view of a meshed container 200A. FIG. 12 is an example of a manufacturing device of the absorbent core used in the absorbent article according to the present invention. FIG. 13 is a plan view of an absorbent core according to a modification of the third embodiment. FIG. 14 is a 3-D contour plot of a groin area of an adult woman.

1. Overview

An absorbent article according to the present invention is, as shown in FIG. 8, for example, an absorbent article 1 having a flat elongated shape that includes: a top sheet 2 that is at least partially liquid permeable; a back sheet 3 that is liquid impermeable; and a liquid retentive absorbent core 4 that has an elongated shape and is disposed between the top sheet 2 and the back sheet 3. The absorbent core 4 is disposed along a virtual center line (hereinafter referred to as "center line CL") that equally divides the absorbent article 1 in a width direction. The absorbent core 4 includes a plurality of first bending regions 10 having a linear shape or a curved shape, of which a bending stiffness is less than an average bending stiffness of the absorbent core 4 and less than a bending stiffness of an adjacent region. The plurality of first bending regions 10 is formed to be substantially symmetrical across the center line CL in the width direction.

In addition, as shown in FIG. 1 or FIG. 8, the plurality of first bending regions 10 is formed dominantly in end portions of the absorbent core 4C in the longitudinal direction.

Furthermore, as shown in FIG. 1, at least in an end of the absorbent core 4C in a longitudinal direction, the first bending regions 10 include a first bending region that is disposed such that an end thereof on a central side in the longitudinal direction is located on an outer side in the width direction and an end thereof on an outer side in the longitudinal direction is located on a central side in the width direction.

The first bending region 10, which is formed on a back side in the longitudinal direction (a side that is positioned on a back side of a wearer's body during use) and in an outer region in the width direction of the absorbent core 4A, is formed so as to be disposed separately from the center line CL in the width direction as approaching a center in the longitudinal direction. On the other hand, the first bending region 10 that is formed on a central side in the width direction is formed so as to approach the center line CL in the width direction as approaching a center in the longitudinal direction.

At least a part of the plurality of first bending regions 10 is formed so as to make the absorbent article 1 deformable along with a shape of an applied part (for example, a wearer's body). For example, with reference to an image 80 shown in FIG. 14 that visualizes the concave and convex portions in a wearer's body, at least a part of the plurality of first bending regions 10 is formed along with a predetermined contour line among a plurality of contour lines 800 that represent the concave and convex portions.

The sum of surface areas of the plurality of first bending regions 10 is at least 5% of a surface area of the absorbent core 4C.

In addition, as shown in FIG. 8, the absorbent core 4C further includes a plurality of second bending regions 11 that are formed so as to intersect with the center line CL in the width direction and have a predetermined width in the longitudinal direction. At least a part of a region 110 sandwiched between the plurality of second bending regions 11 in the longitudinal direction can be moved (displaced) in the longitudinal direction. More specifically, the region 110 sandwiched between two second bending regions 11 in FIG. 4 can be moved (displaced) backward in the longitudinal direction by flexion deformation at the second bending regions 11 and 11, as shown in FIG. 5B. Furthermore, the region 110 deforms so as to stand in a thickness direction of the absorbent core, i.e. toward a wearer's body, in accordance with flexion of the absorbent core.

As shown in FIG. 8, a basis weight of the first bending region 10 or of the second bending region 11 is lower than an average basis weight of the absorbent core 4C and lower than a basis weight of an adjacent region.

More specifically, in a case where the absorbent core 4 is obtained by covering an absorbent member including a pulp and/or polymer absorbent body with a liquid permeable sheet, a basis weight of the absorbent member in the first bending region 10 or in the second bending region 11 is lower than an average basis weight of the absorbent member in the absorbent core 4 and lower than a basis weight of the absorbent member in an adjacent region.

In addition, the absorbent article 1 is foldable. As shown in FIGS. 7 and 8, third bending regions 12 and 12 are formed on the absorbent core 4C at positions corresponding to folding positions F and B. Two third bending regions 12 and 12, which are disposed to be separated from each other in the longitudinal direction, are formed on the absorbent core 4C. In a case where the absorbent core 4C is compartmented by the two third bending regions 12 and 12 into a central portion, a front portion that is disposed on a front side of a wearer's body during use, and a back portion that is disposed on a back side of a wearer's body during use, a compressed groove can be formed continuously from a predetermined position in the central portion to a predetermined position in the back portion as in an absorbent core 4E shown in FIG. 13, which is a modification of the absorbent core 4C. Conditions such as bending stiffness and basis weight for the third bending region 12 are similar to that of the first bending region and the second bending region.

Furthermore, an absorbent core including a plurality of first bending regions having a linear shape or a curved shape, of which bending stiffness is less than an average bending stiffness and less than a bending stiffness of an adjacent region, can be manufactured by accumulating a fiber including cellulosic fiber in a container 200, in which a plurality of convex portions 210 and the like are formed, which are shown in FIG. 9.

2. Embodiments

Embodiments of the absorbent article and the absorbent core according to the present invention are described hereinafter with reference to FIGS. 1 to 14.

2.1. Absorbent Core 2.1.1. First Embodiment

An absorbent core 4A according to a first embodiment is described hereinafter with reference to FIGS. 1A and 1B. As shown in FIG. 1A, the composite sheet 4A is an absorbent core having a substantially flat and elongated shape, on which the plurality of first bending regions 10 is formed. The plurality of first bending regions 10 has a bending stiffness less than an average bending stiffness of the absorbent core 4A and less than a bending stiffness of an adjacent region. Although the first bending region 10 is formed in a curved shape in FIG. 1, the shape is not limited thereto and can also be linear. The plurality of first bending regions 10 are formed to be substantially symmetrical across the center line CL equally dividing the absorbent core 4A in the width direction.

A region Z shown on the absorbent core 4A is a region that is brought into contact with an excretory part such as the vaginal opening. In a predetermined region including the region Z, which is brought into contact with the groin in a case where an absorbent article including the absorbent core 4A is worn on the wearer's body, the first bending region 10 is not formed. As shown in FIG. 1A, the plurality of first bending regions 10 is formed dominantly in end portions of the absorbent core 4A in the longitudinal direction. Since the first bending region 10 is not formed in a region that is brought into contact with the groin, leakage of menstrual blood and the like, due to unexpected deformation of the absorbent core 4A in the groin, can be inhibited.

The plurality of first bending regions 10 is formed so as to make the absorbent core 4A deformable along with a shape of the wearer's body as an applied part of the absorbent core 4A.

The first bending region 10 is formed by, for example, providing a slit on the absorbent core 4A. The first bending region 10 can be formed, for example, such that a position and a shape thereof follow a predetermined contour line among a plurality of contour lines that represent heights of concave and convex portions in an image that visualizes the concave and convex portions on an applied part (shown in FIG. 14, described later).

FIG. 14 is a 3-D contour plot of a groin area of an adult woman, taken by a contactless 3-D digitizer "VIVID 910" (manufactured by Konica Minolta Sensing, Inc.). The subject was a woman with a BMI of 21 (standard proportions) and the image was taken of the subject lying on her back. The BMI (Body Mass Index) value is a ratio of body weight to the square of body height (body weight (kg)/(body height (m))2), and represents a physical constitution. As shown in FIG. 14, trajectories in the 3-D contour plot are greatly different in front of and behind the vaginal opening Z. The trajectories have a substantially inverted V-shape in front of the vaginal opening Z (on a front side) due to a swelling shape of the pubic mound, and have a substantially V-shape behind the vaginal opening Z (on a back side) due to the groove shape of inner thigh and buttocks.

As shown in FIG. 1, the first bending region 10, among the plurality of first bending regions 10, which is formed in an outer region in the width direction of the absorbent core 4A, is formed so as to be disposed separately from the center line CL in the width direction as approaching a center in the longitudinal direction of the absorbent core 4A. On the other hand, the first bending region 10, which is formed on a center region in the width direction and disposed more on the back side than the abovementioned first bending region 10 formed on an outer side in the width direction, is formed so as to approach the center line CL in the width direction as approaching a center in the longitudinal direction.

By thus forming the plurality of first regions 10, for example, a front portion disposed in front of an excretory part such as the vaginal opening (front side of the wearer's body) during use is deformed to a concave shape along the swelling shape of the pubic mound, and a back portion disposed behind an excretory part such as the vaginal opening (back side of the wearer's body) during use is deformed to a convex shape along a shape of the inner thigh and buttocks. In addition, as the first bending region 10 that is formed on a central side in the width direction is formed so as to approach the center line CL in the width direction as approaching a center in the longitudinal direction, an adjacent region of the first bending region 10 in a side end portion in a center in the longitudinal direction is deformed to project toward the wearer's body.

The length of the first bending region 10 formed by slit processing is, for example, 5 to 50 mm and more preferably 10 to 30 mm, and the width thereof is 0 to 3 mm and more preferably 0 to 2 mm. The depth of the first bending region 10 formed by slit processing in the thickness direction is not particularly limited, and the first bending region 10 can be either cut through (penetrating) or halfway cut (not penetrating) on the absorbent core.

Although slits are formed on the absorbent core 4 in the present embodiment, the slits can also be formed on a material disposed closer to the skin than the absorbent core 4, such as a top sheet and a second sheet (not shown). In addition, the slits can be formed so as to reach a circumference of the absorbent core 4.

Materials and the like constituting the absorbent core 4A are described hereinafter with reference to FIG. 6A or 6B. FIG. 6A shows an absorbent core in which a hydrophilic fiber 410 is accumulated and disposed, being sandwiched between covering sheets 411 and 412. Details thereof are described below.

The hydrophilic fiber may be, for example, celluloses such as pulp and cotton, regenerated celluloses such as rayon and fibril rayon, semi-synthetic celluloses such as acetate and triacetate, particulate polymer, fibrous polymer, thermoplastic hydrophobic chemical fiber, thermoplastic hydrophobic chemical fiber which is hydrophilized, that can be used singly or in combination. Cellulose foam or continuous foam of synthetic resin can be blended into the absorbent core. Alternatively, foam or the sheet-shaped hydrophilic fiber aggregate, which is pulverized and then shaped, can also be used.

The covering sheet 4a can be of any material which is liquid permeable and has barrier properties which prevent the inside hydrophilic fiber from protruding, and an example thereof includes a fabric, a nonwoven fabric, a perforated plastic sheet and the like, without being limited thereto. The material for the woven fabric or the non-woven fabric can be either a natural fiber or a chemical fiber. As the natural fiber, celluloses such as pulverized pulp, cotton and the like can be exemplified. As the chemical fiber, regenerated celluloses such as rayon and fibril rayon, semi-synthetic celluloses such as acetate and triacetate, thermoplastic hydrophobic chemical fiber, and thermoplastic hydrophobic chemical fiber which is hydrophilized and the like can be exemplified.

As a manufacturing method of the non-woven fabric, web foaming of dry type (carding process, spun bond process, melt blown process, air-laid process, or the like), wet type, or a combination thereof can be adopted. In addition, as a method of bonding, thermal bonding, needle punch, chemical bonding, and the like can be exemplified, without being limited thereto. Alternatively, a spun lace formed in a sheet-like shape by spun-lace process may be used.

As a preferred embodiment, an absorbent core 4 can be exemplified that has a fiber basis weight of 100 g/m² to 2000 g/m², and a bulk of 1 mm to 50 mm, which can be obtained by mixing pulp in the range of 80% to 100%, and particulate polymer in the range of 20% to 0%, and then covering with a tissue, followed by an embossing finish in order to obtain a sheet-shape. The embossing finish is for preventing the absorbent core 4 from losing its shape and an embossing area ratio is preferably in the range of 10% to 100%, and more preferably 30% to 80%.

Figure 6B:
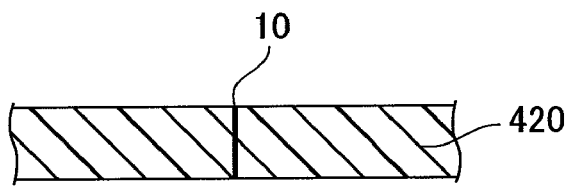
FIG. 6B is a cross-sectional view of the absorbent core.

FIG. 6B shows an embodiment using an air-laid sheet as an absorbent core. In the absorbent core shown in FIG. 6B, unlike in FIG. 6A, the covering sheet is not disposed.

As an air-laid sheet 420, an absorption sheet and a polymer sheet into which a polymer is blended can be exemplified. The thickness of the air-laid sheet 420 is, for example, preferably 0.3 to 5 mm. The hydrophilic fiber exemplified in the absorbent core shown in FIG. 6A can be used as a material for the absorption sheet, and an example of the absorption sheet includes: an absorbent paper; a non-woven fabric; and a sheet obtained by processing fiber with a binder. In addition, the hydrophilic fiber exemplified in the absorbent core shown in FIG. 6A and a polymer can be used as materials for the polymer sheet, and examples of the polymer sheet include a sheet obtained by blending and shaping the materials. In the sheet thus obtained, for example, particulate polymer may be dispersed in layers or in a three dimensional way.

The slits on the absorbent core can be formed, for example, by passing the absorbent core between a roller on which slit blades are disposed in a predetermined pattern and a flat roller.

2.1.2. Second Embodiment

A composite sheet 4B according to a second embodiment is described hereinafter with reference to FIGS. 2 to 5. As shown in FIGS. 2A and 2B, the absorbent core 4B includes a plurality of first bending regions 10 as in the absorbent core 4A according to the first embodiment. Although a forming pattern of the first bending region 10 on the absorbent core 4B according to the present embodiment is similar to a forming pattern of the first bending region 10 on the absorbent core 4A according to the first embodiment, the absorbent core 4B is different from the absorbent core 4A in that the first bending region 10 has a width (lateral length) and a material constituting the absorbent core 4 is not disposed in the first bending region 10.

In addition, the absorbent core 4B is different from the absorbent core 4A in that two second bending regions 11 and 11 are formed behind the region Z, which is in contact with an excretory part such as the vaginal opening, in the longitudinal direction. As a result, in a case where the absorbent core 4B deforms as shown in FIG. 4, the second bending regions 11 and 11 are crushed in the width direction thereof as shown in FIGS. 5A and 5B and a center portion in each of the second bending regions 11 and 11 is displaced forward in the longitudinal direction and deformed by flexing. This displaces a region 110 between the second bending regions 11 in the longitudinal direction (for example, toward a front side).

FIG. 3 is a diagram showing a cross-sectional shape of a human body taken by MRI (Magnetic Resonance Image), and shows that a curvature is sharply increased from behind the vaginal opening Z on a line 510 that connects the vaginal opening Z and coccygeal bone Y, in a center of the body.

The absorbent core 4B includes the second bending regions 11 and 11 formed on a back portion thereof, in order to deform a central portion and the back portion that are deformed into a convex shape in the thickness direction (to bend a convex portion) along such a body shape. This can move (displace) the region 110 in the longitudinal direction, thereby allowing the absorbent core 4B to be deformed along the wearer's body shape, in a state of being deformed into a convex portion in the thickness direction. Here, a migration length of the region 110 is, for example, 1 to 20 mm, and more particularly 2 to 10 MM.

In addition, the absorbent core 4B further includes third bending regions 12 and 12 formed at positions corresponding to folding positions F and B of an absorbent article including the absorbent core 4B. Although the third bending regions 12 and 12 are explained regarding an absorbent core 4C described later, the third bending regions 12 and 12 are similar to the first bending region 10 and the second bending region 11, except for a position thereof.

A length (longitudinal dimension) of each of the first bending region 10 or the second bending region is, for example, in the range of 5 to 50 mm and preferably in the range of 10 to 30 mm; and a width (transverse dimension) thereof is in the range of 1 to 10 mm and preferably in the range of 2 to 5 mm. In addition, as a planar shape of the first bending region 10 or the second bending region 11, a circle, an ellipse, a square, a rectangle, a triangle and the like can be exemplified.

Furthermore, a surface area of the first bending region 10 or the second bending region 11 is at least 5 mm², particularly 5 to 500 mm², and more particularly 50 to 200 mm²; and a surface area ratio of the bending region (for example the first bending region 10) is at least 5%, particularly 5 to 50%, and more particularly 10 to 40% of a surface area of the absorbent core 4B. By providing the first bending region 10 and the second bending region 11 having the abovementioned dimensions and the like, the absorbent core can be deformed along with a shape of an applied part thereof, while being kept from losing its shape and the like due to a deformation unrelated to the shape of an applied part.

Figure 6C:
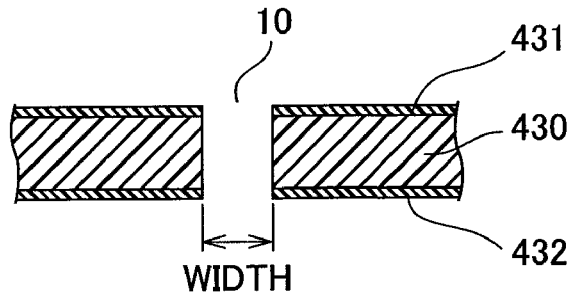
FIG. 6C is a cross-sectional view of the absorbent core.
Figure 6D:
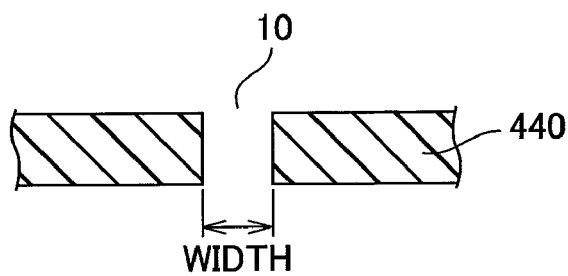
FIG. 6D is a cross-sectional view of the absorbent core.

As the first bending region 10 in the absorbent core 4B, the first bending region 10 shown in FIG. 6C or 6D can be exemplified. Here, FIG. 6C shows a configuration for an absorbent core in which a hydrophilic fiber 430 is accumulated and disposed, being sandwiched between covering sheets 431 and 432. In addition, FIG. 6D shows a configuration in which the first bending region 10 and the like is formed on an air-laid sheet. The hydrophilic fiber and the like are described above in detail.

An example of a manufacturing method for the absorbent core 4B shown in FIG. 6C or 6D, on which the first bending region 10 not including a material constituting the absorbent core such as a hydrophilic fiber is formed, is described hereinafter. For example, a method can be exemplified in an absorbent core is first formed having a uniform basis weight and a uniform thickness, and then a predetermined pattern out of the absorbent core is cut out. More specifically, an absorbent core, having the first bending region 10 not including a material constituting the absorbent core, can be manufactured by passing the absorbent core between a roller, on which slit blades of a predetermined shape having a width are disposed in a predetermined pattern, and a flat roller.

Figure 6E:
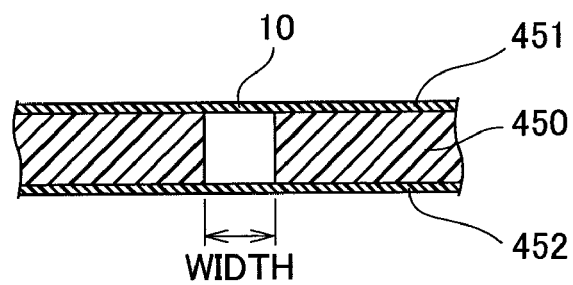
FIG. 6E is a cross-sectional view of the absorbent core.

In addition, as the first bending region 10 in the absorbent core 4B, the first bending region 10 having tissues 451 and 452 above and below, as shown in FIG. 6E, can be exemplified. In the absorbent core shown in FIG. 6E, an entire circumference of a pulp 450 is covered by the tissues 451 and 452, also covering the first bending region 10 from above and below. Although a cross-sectional shape of the first bending region 10 is rectangular, the shape is not limited thereto and can also be a tapered trapezoidal shape, a diamond shape, and triangular, for example.

An example of a manufacturing method for the absorbent core 4B, on which the first bending region 10 not including the pulp 450 covered by the tissues 451 and 452 are formed as shown in FIG. 6E, is described hereinafter. For example, as shown in FIG. 9, by installing a meshed container 200 in which convex portions 210 are formed in a predetermined pattern on a suction drum 920 shown in FIG. 12, a pulp 901 opened by an opening portion 910 and a polymer, not accumulated in the convex portions 210 and the like in the meshed container 200, are transferred onto a tissue unreeled from a roll of tissue 903 in a predetermined direction.

As a result, the convex portions 210 in the meshed container 200 form the first bending regions 10, convex portions 211 form the second bending regions 11, and convex portions 212 form the third bending regions 12. Here, even if the pulp and the polymer are accumulated on the convex portions 210 and the like in the meshed container 200, a scuffing roller 930 shown in FIG. 12 can scrape and remove the pulp and the polymer.

In addition, the convex portions 210 and the like in the meshed container 200 are preferably air impermeable at least in part (for example, at an apex or an entirety of the convex portion). For example, mesh in the convex portions 210 can be plugged with a resin and the like; a tape, a metallic plate and the like can be disposed on a surface of the convex portions 210; or the convex portions 210 can be formed of a material that is not air permeable such as rubber.

The convex portions 210 and the like can be formed, for example, in accordance with a shape of the first bending region 10 and the like. For example, as shown in FIG. 10, as a cross-sectional shape thereof in a planar direction, a rectangle can be exemplified, and as a cross-sectional shape in a direction perpendicular to the planar direction, a tapered trapezoidal shape can be exemplified.

The length of the convex portions 210 and the like is, for example, 5 to 50 mm and more preferably 10 to 30 mm, and the width thereof is 1 to 10 mm and more preferably 2 to 5 mm. The height of the convex portions 210 and the like can be determined in accordance with a basis weight of the absorbent core 4. In a case where a basis weight of the pulp and the polymer is in a range of 50 to 2000 $g/m^2$, the height of the convex portions 210 and the like is 1 to 20 mm, and, in a case where the basis weight of the pulp and the polymer is in a range of 50 to 800 $g/m^2$, the height of the convex portions 210 and the like is 1 to 5 mm.

The convex portion 210 is formed to have a tapered trapezoidal shaped cross section, as shown in FIGS. 9 and 10, in order to smoothly transfer the pulp and the polymer, which is captured by the suction drum 920 shown in FIG. 12, onto a tissue while keeping a shape thereof.

In addition, by providing a plurality of convex portions 210 in the meshed container 200 and forming the abovementioned air-impermeable portions, the first bending regions 10 and the like can be formed. It should be noted that a basis weight of the pulp and the polymer is preferably in a range of 50 to 500 $g/m^2$, since a pulp and a polymer having a high basis weight easily accumulate on the air-impermeable portion.

Figure 6F:
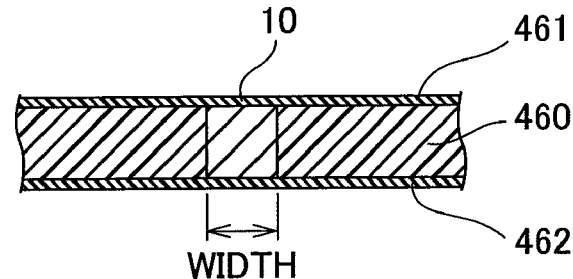
FIG. 6F is a cross-sectional view of the absorbent core.

As the first bending region 10 on the absorbent core 4B, an embodiment of FIG. 6F can be exemplified. A point which is different from that of FIG. 6E is the presence of the pulp and the polymer in the first bending region 10. A basis weight of the pulp and the like in the first bending region 10 is no greater than 80%, particularly 1 to 80%, and more particularly 5 to 30%, of the basis weight of the pulp in an adjacent region.

In addition, a manufacturing method in the embodiment of FIG. 6F is different from the manufacturing method in the aspect of FIG. 6E in that the scuffing roller 930 shown in FIG. 12 is not provided and the air-impermeable portions are not provided to the convex portions 210 in the meshed container 200.

2.1.3. Third Embodiment

A composite sheet 4C according to a third embodiment is described hereinafter with reference to FIGS. 7 to 10. As shown in FIG. 7A, 7B, or 8, the composite sheet 4C has a structure similar to that of the absorbent core 4B according to the second embodiment, in which the first bending region 10 is further provided between the second bending regions 11 and 11 in the absorbent core 4B. In other words, the absorbent core 4C includes, as the absorbent core 4B, a plurality of first bending regions 10 and two second bending regions 11. In addition, the absorbent core 4C also includes the third bending regions 12 and 12 formed at positions corresponding to folding positions F and B of an absorbent article including the absorbent core 4C.

In other words, on the absorbent core 4C, the third bending regions 12 and 12 for facilitating folding are formed at positions corresponding to positions F and B corresponding to folding positions of an absorbent article 1 including the absorbent core 4C in a state of being folded with the top sheet inside. The third bending region 12 is formed to have a bending stiffness lower than an average bending stiffness of the absorbent body 4C and than a bending stiffness of an adjacent region thereof. In addition, the third bending region 12 is formed to have a basis weight lower than an average basis weight of the absorbent body 4C and than a basis weight of an adjacent region thereof. Here, the first bending region 10 and the second bending region 11 are as described above.

As a result, by forming the third bending regions 12 and 12 at positions F and B corresponding to folding positions, the absorbent article 1 including the absorbent core 4C becomes easy to fold. Moreover, since a bent retention due to a cellulosic fiber and the like included in the absorbent body 4C can be thus decreased, the folded sanitary napkin 1 can be easily opened out to be flat.

The absorbent core 4C can be manufactured in a similar method to the abovementioned manufacturing method of the absorbent core 4B. A meshed container, in which convex portions corresponding to the first bending regions 10 and the like in the absorbent core 4C are disposed, is used.

Subsequently, modifications to the absorbent core 4C are described with reference to FIGS. 11 and 13. An absorbent core 4D as a first modification is different from the absorbent core 4C in that a central portion projects in a thickness direction. The absorbent core 4D can be manufactured by the abovementioned method using a meshed container 200A, which is shown in FIG. 11, in which a concave portion 220 is formed in a central region thereof.

An absorbent core 4E as a second modification has compressed grooves 610 and 610 formed in the longitudinal direction, as shown in FIG. 13. In particular, the compressed grooves 610 are formed continuously from a predetermined position in the central portion to a predetermined position in the back portion, given that the absorbent core 4E is divided by the two third bending regions 12 into a front portion, the central portion, and the back portion.

The compressed groove 610 can be either a so-called hinge (leak-proof groove) that is formed on the top sheet and on the absorbent core 4E, or a so-called absorbent core emboss that is formed only on the absorbent core 4E.

In addition, the compressed groove 610 is only required to have a high stiffness in order to allow the back portion to easily deform into a convex shape, following the central portion of the absorbent core 4 that deforms into a convex shape. As the compressed groove 610, a compressed groove in which a high compression portion and a low compression portion are alternately disposed can be exemplified.

Furthermore, as an overall shape of the compressed groove 610, a linear shape, a curved shape, a corrugated shape and the like in the longitudinal direction of the absorbent core 4E (an absorbent article) can be exemplified. Moreover, the compressed grooves 610 and 610 can be formed to project toward a side opposite to a wearer's body side, in order to stabilize convex deformation.

Since the pair of compressed grooves 610 and 610 is thus formed continuously from the central portion to the back portion of the absorbent core 4E, in a case where the central portion deforms into a convex shape in a thickness direction due to a compressive force from the inner thigh, for example, the back portion can easily deform into a convex shape following the deformation in the central portion. As a result, in an absorbent article including the absorbent core 4E, the back portion can easily deform into a convex shape following the deformation in the central portion, in a case where the central portion deforms into a convex shape in a thickness direction due to a compressive force from the inner thigh.

3. Absorbent Article

An embodiment of the absorbent article according to the present invention is described hereinafter with reference to FIG. 8. As shown in FIG. 8, the absorbent article 1 is an absorbent article having a flat and elongated shape and includes: a top sheet 2 that is at least partially liquid permeable; a back sheet 3 that is liquid impermeable; and an absorbent core 4C having an elongated shape that is disposed along the longitudinal direction between the top sheet 2 and the back sheet 3.

As a shape of the absorbent article 1 seen from one side, a rectangular shape, an elliptical shape, a guitar shape, and the abovementioned shapes with a so-called wing and the like can be exemplified; however, the shape is not particularly limited thereto and can be any shape suitable for a shape of a woman's body and underwear.

Regarding the overall dimensions of the outer shape thereof, a length in the longitudinal direction is preferably 100 to 500 mm, and more preferably 150 to 350 mm. In addition, a length thereof in the width direction (lateral direction) is preferably 30 to 200 mm, and more preferably 40 to 180 mm.

For example, an embossing pattern or a compressed groove (a so-called hinge, a leak-proof groove) that represents a groin shape can also be formed on the top sheet 2 and the absorbent core 4, in order to make the absorbent article 1D easy to deform along the groin shape of the wearer's body, which is an applied part. The compressed groove can act as the abovementioned compressed groove 610.

A sheet-shaped member of a liquid permeable structure, such as a woven fabric, a non-woven fabric, and a perforated plastic sheet, can be used as the top sheet 2, without being particularly limited.

As the back sheet 3, a film composed mainly of PE, PP and the like, an air-permeable resin film, a sheet obtained by joining an air-permeable resin film with a non-woven fabric such as spun bond or spun lace, a multilayer of SMS, or the like can be suitably used.

The top sheet 2, the absorbent core 4, and the back sheet 3 are preferably joined with each other, in order to prevent delamination in each thereof. In addition, the top sheet 2 and the back sheet 3 are preferably joined at a circumferential edge of the absorbent core 4, so as to seal in the absorbent core 4.

In a case where the absorbent core 4 is obtained by sandwiching a hydrophilic fiber with covering sheets, the absorbent core can be embossed in order to keep a shape and avoid twisting thereof during use, and to adjust a thickness thereof, although this is not required in a case where an air-laid sheet is used as the absorbent core 4.

The absorbent core 4 can be embossed, after forming bending regions such as the first bending region 10, by passing between an embossing roller having a pattern thereon and a flat roller. The pattern on the embossing roller can be selected from a reticular pattern, a dot pattern, an undulating pattern and the like, and is preferably a reticular pattern in order to prevent breakage of the covering sheet due to an embossing pattern entering the bending region.

The preferred embodiments described above are merely used as examples of the present invention, and are not intended to be limiting. Modifications such as additions, omissions and the like can be made within the scope of the present invention. Therefore, the present invention is not to be determined and limited by disclosures in the specification, and is limited only by the scope of the claims.

The invention claimed is:

1. An absorbent article having a width direction and a longitudinal direction that is orthogonal to the width direction, said article comprising:
    a top sheet that is at least partially liquid permeable;
    a back sheet that is liquid impermeable; and
    an absorbent core that has an elongated shape along the longitudinal direction and is disposed between the top sheet and the back sheet, the absorbent core including a front portion, a back portion and a central portion between the front portion and the back portion in the longitudinal direction,
    wherein a dimension of the central portion in the width direction is narrower than that of each of the front portion and the back portion in the width direction,
    wherein the absorbent core includes a plurality of first bending regions having a bending stiffness less than an average bending stiffness of the absorbent core and less than a bending stiffness of an adjacent region of the absorbent core, and
    wherein the plurality of first bending regions is arranged substantially symmetrical across a center line equally dividing the absorbent article in the width direction and is arranged only in the front portion and the back portion of the absorbent core,
    wherein each of the plurality of first bending regions penetrates through the absorbent core from a side of the top sheet to a side of the back sheet, and
    wherein each of the plurality of first bending regions is free of absorbent material or has a basis weight lower than an average basis weight of the absorbent core.

2. The absorbent article according to claim 1, wherein the absorbent core further comprises a plurality of second bending regions that intersects with the center line in the width direction and has a predetermined width in the longitudinal direction, and wherein a region between the second bending regions adjacent to each other in the longitudinal direction is displaceable in the longitudinal direction to allow the absorbent core to be deformable in a thickness direction.

3. The absorbent article according to claim 1, wherein in at least one of the front and back portions of the absorbent core, the plurality of first bending regions is inclined with respect to the center line in the longitudinal direction.

4. The absorbent article according to claim 2, wherein at least one of the second bending regions is elongated in the width direction and is located between the two adjacent first bending regions in the width direction.

5. The absorbent article according to claim 2, wherein at least one of the first bending regions is arranged at the region which is between the adjacent second bending regions and the at least one of the first bending regions is independently arranged from the adjacent second bending regions in the longitudinal direction.

6. The absorbent article according to claim 2, further comprising third bending regions on the absorbent core at folding lines along which the absorbent core is foldable, wherein said third bending regions intersect the center line of the absorbent core.

7. The absorbent article according to claim 2, wherein each of the second bending regions has a center area displaceable forward in the longitudinal direction and deformable by flexing.

8. The absorbent article according to claim 3, wherein the plurality of first bending regions includes in the front portion, at least one bending region curving inwardly while extending toward the center line from a back side to a front side in the longitudinal direction, in the back portion, at least one bending region curving outwardly while extending away from the center line from the back side to the front side in the longitudinal direction, and in the back portion, at least one bending region curving inwardly while extending toward the center line from the back side to the front side in the longitudinal direction.

9. The absorbent article according to claim 3, wherein the plurality of first bending regions includes in the front portion, at least one bending region extending toward the center line from a back side to a front side in the longitudinal direction, and in the back portion, at least one bending region extending away from the center line from the back side to the front side in the longitudinal direction.

10. The absorbent article according to claim 1, wherein said first bending regions are slits.

11. The absorbent article according to claim 2, further comprising a pair of compressed grooves extending continuously from the central portion into the back portion of the absorbent core and between the first bending portions and the second bending portions, so that the central portion and the back portion become deformable into a convex shape in the thickness direction in use.

12. The absorbent article according to claim 1, wherein the absorbent core further comprises a predetermined region adapted to be in direct contact with an excretory part of a wearer in use, said predetermined region located in the central portion and free of the plurality of the first bending regions.

13. The absorbent article according to claim 1, wherein the absorbent core further comprises a predetermined region adapted to be in direct contact with an excretory part of a wearer in use, said predetermined region located in the central portion and free of the plurality of the first bending regions, at least one of the first bending regions in the front portion is forward of the predetermined region and curves outwardly away from said predetermined region while extending from a front side to a back side in the longitudinal direction, and all of the first bending regions in the back portion are backward of the predetermined region and curve outwardly away from said predetermined region while extending from the back side to the front side in the longitudinal direction.

14. The absorbent article according to claim 13, further comprising a plurality of second bending regions which intersects with the center line of the absorbent core in the width direction is arranged in the back portion backward of the predetermined region and between two adjacent first bending regions.

15. The absorbent article according to claim 14, further comprising third bending regions which are elongated in the width direction and intersect the center line of the absorbent core, wherein at least one of the third bending regions is arranged forward of the predetermined region, and at least one of the third bending regions is arranged backward of the predetermined region.

16. The absorbent article according to claim 1, wherein one of the first bending regions includes opposite ends, one end of said first bending region on a central side in the longitudinal direction is located on an outer side in the width direction, and the other end of the first bending region on an outer side in the longitudinal direction is located on a central side in the width direction.

17. An absorbent article having a width direction and a longitudinal direction that is orthogonal to the width direction, said article comprising:

a top sheet that is at least partially liquid permeable;

a back sheet that is liquid impermeable; and an absorbent core that has an elongated shape along the longitudinal direction and is disposed between the top sheet and the back sheet, the absorbent core including a front portion, a back portion and a central portion located between the front portion and the back portion in the longitudinal direction, wherein a dimension of the central portion in the width direction is narrower than that of each of the front portion and the back portion in the width direction, wherein the absorbent core includes a plurality of first bending regions each of which has a bending stiffness less than an average bending stiffness of the absorbent core and less than a bending stiffness of an adjacent region of the absorbent core, wherein the plurality of first bending regions is arranged substantially symmetrical across a center line equally dividing the absorbent article in the width direction and is arranged only in the front portion and the back portion of the absorbent core, and wherein each of the plurality of first bending regions is free of absorbent material from a side of the top sheet to a side of the back sheet.

* * * * *